(12) United States Patent
Hori (10) Patent No.: US 6,529,581 B2
(45) Date of Patent: Mar. 4, 2003

(54) RADIATION IMAGE TAKING APPARATUS

(75) Inventor: Naoyuki Hori, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/863,367

(22) Filed: May 24, 2001

(65) Prior Publication Data

US 2001/0053200 A1 Dec. 20, 2001

(30) Foreign Application Priority Data

Jun. 6, 2000 (JP) .......................................... 2000-168936

(51) Int. Cl.$^7$ ................................................. G21K 1/00
(52) U.S. Cl. ..................................... 378/154; 378/98.8
(58) Field of Search ................. 378/154, 155, 378/98.8

(56) References Cited

U.S. PATENT DOCUMENTS 5,666,395 A * 9/1997 Tsukamoto ................. 378/154
5,801,385 A * 9/1998 Endo et al. ................. 378/98.8
6,229,877 B1 * 5/2001 Agano ........................ 378/98.2

* cited by examiner

Primary Examiner—Craig E. Church
(74) Attorney, Agent, or Firm—Kanesaka & Takeuchi

(57) ABSTRACT

When X-rays are projected to an X-ray sensor through a grid, a pitch of slits on the grid has a relationship such that a length obtained by multiplying an odd number to a half pitch of a projection image on the X-ray sensor is equal to a pitch of detection pixels of the X-ray sensor. X-rays passing through a sample to be measured via the grid are detected by the X-ray sensor. Levels of the detected X-ray detection signals are inputted into an operation process portion and subjected to an equalizing process for every pixel groups, each having even number of the detection pixels, continuously lined up in a pitch direction of the grid. As a result, irregularities of the levels of the X-ray detection signals can be corrected, and moires generated on an output screen of an image display portion can be removed.

6 Claims, 8 Drawing Sheets

RADIATION IMAGE TAKING APPARATUS

BACKGROUND OF THE INVENTION AND RELATED ART STATEMENT

The invention relates to a radiation image taking apparatus to be used in a medical field, industrial field and the like, and more particularly, it relates to a technique for removing moires generated on an output screen when the detected results are outputted.

A conventional radiation image taking apparatus includes a grid provided with a number of slits on an entering side of radiations of a radiation detection pixel matrix to remove dispersion rays contained in X-rays passing through a sample to be measured.

When X-rays passing through the sample to be measured pass through the grid, since the dispersion rays are shut off by the grid, it is possible to prevent an image quality from being lowered by the dispersion rays. However, in case there are gaps of pitches between the slits provided on the grid and the detection pixels, respectively, irregularities in the detected radiation signals are generated to thereby generate moires on a screen of an image displaying device. In such a case, the following methods have been taken.

As a fist method, a grid is formed accurately such that pitches of the slits disposed on the grid are the same as those in the radiation detection pixel matrix, and the grid is located close to the radiation detection pixel matrix or integrally formed therewith.

As a second method, a grid is positioned close to a one-dimensional or two-dimensional radiation detection pixel matrix, and is horizontally swung or moved in a pitch direction of the grid with respect to the radiation detection pixel matrix so that projection images projected through the grid are uniformly projected to the respective positions on the radiation detection pixel matrix.

Further, as a third method, when a motion image is taken, prior to a measurement, levels of the radiation detection signals of the respective detection pixels are measured beforehand, and a position of the grid is set so that the detecting levels of the respective detection pixels become substantially uniform. In other words, if necessary, the grid is fixed with a proper inclination angle with respect to the radiation detection pixel matrix.

However, the conventional radiation image taking apparatus having the structure as described above has the following problems.

Figure 7:
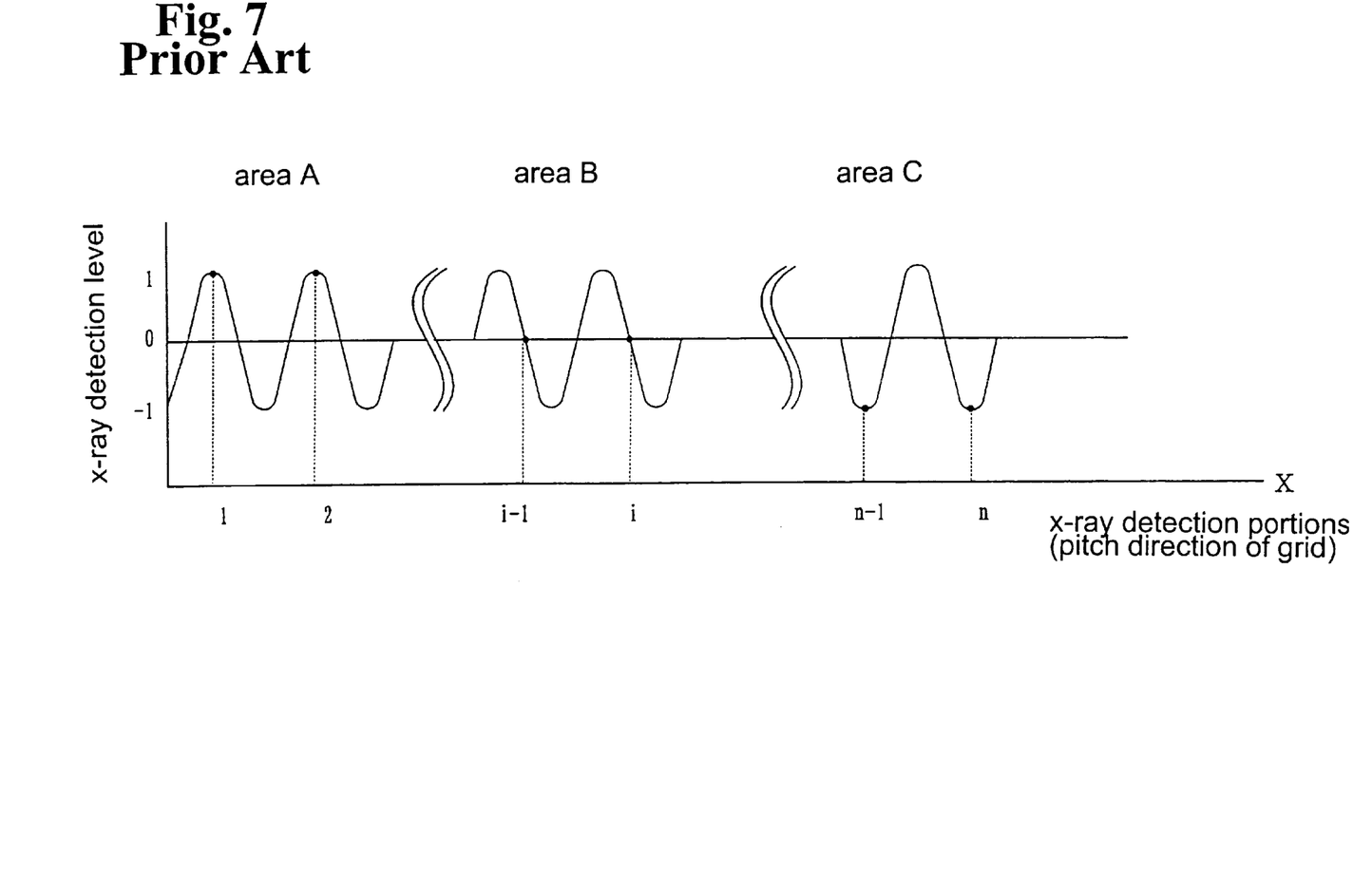
FIG. 7 is a graph showing X-ray detection signals detected by a conventional radiation image taking apparatus.
Figure 8:
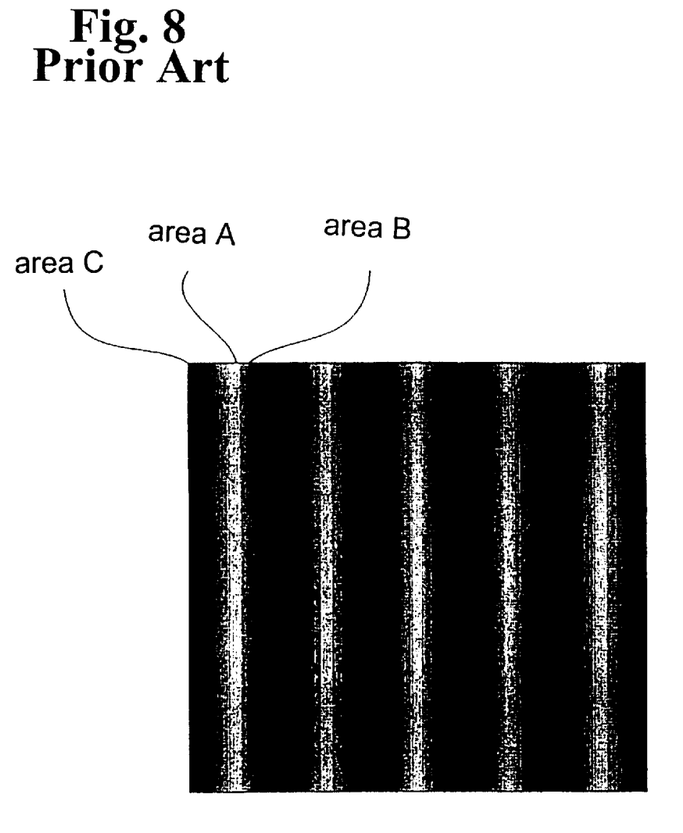
FIG. 8 is an output image outputted from the conventional radiation image taking apparatus.

In the first method where the grid having the high pitch accuracy is disposed close to the radiation detection pixel matrix or integrally formed therewith, it is extremely difficult to accurately form the pitches of the slits formed on the grid. Therefore, in case there is a fine error in the pitch accuracy of the manufactured grid, as shown in FIG. 7, toward a pitch direction of the grid, i.e. plus direction on an X-axis in the drawing, the detection pixels and slit positions of the grid do not match their positions gradually. In other words, in an area A in FIG. 7, since there is no gap between the slit of the grid and the detection pixel, an X-ray detecting signal (+)1 is detected from the detection pixel. However, as it comes to the pitch direction of the grid, due to the gaps between the slit disposed on the grid and the detection pixel, the X-ray detection signals detected from the detection pixel become zero (0) in an area B and (−)1 in an area C. As apparent from the above, the level changes of the X-ray detecting signals detected at the detection pixels are repeated according to the gaps of the positions of the slits on the grid and positions of the detection pixels. As a result, as shown in FIG. 8, there arises a problem where the gaps appear as moires on a displaying screen.

In the second method where the grid is swung or moved, when a moving image is taken, the swinging or movement of the grid must correspond to an image taking mode of 30 frames/second to obtain a smooth moving image. That is, a high speed swinging unit of one several millionths in a second is required in order that the swinging of the grid corresponds to the image-taking mode. Therefore, it is very difficult to remove moires by the movement when the moving image is taken. Also, since a large apparatus is necessary to swing or move the grid, there is a problem of obtaining an installation place of the apparatus and an economical burden.

In the third method, the radiation detecting signals of the respective radiation detection pixels disposed in a matrix shape are measured beforehand and the grid has to be set at a position where the radiation detection signals of the respective pixels become uniform, which results in an operational burden to an operator. Also, since it is necessary that the grid is positioned with a three dimensional inclination in horizontal and vertical directions with respect to the radiation detection pixel matrix, a larger apparatus is required, which is uneconomical.

In view of the above defects, an object of the present invention is to provide a radiation image taking apparatus for removing moires from a detected image without using a grid with high accuracy.

Further objects and advantages of the invention will be apparent from the following description of the invention.

Summary of the Invention

The present invention has the following structure in order to attain the above-stated object.

A radiation image taking apparatus according to a first aspect of the invention includes a radiation irradiation device for irradiating radiations to a sample to be measured; a grid having a number of slits for allowing the radiations to pass therethrough to remove dispersion rays from the radiations passed through the sample to be measured; a radiation detecting device wherein detection pixels for detecting radiations passing through the grid are arranged in a one-dimensional or two-dimensional matrix shape; and an image output device for outputting a detected image. In the invention, pitches of the slits of the grid are set to have such a relationship that when X-rays are projected to the radiation detecting device through the grid, a length obtained by multiplying odd-number to a half pitch of the projection image on the radiation detecting device through the grid is equal to a pitch of detection pixels of the radiation detecting device; and there is provided an operation device where the radiation detection signals obtained from the radiation detecting device are subjected to an equalizing process for every pixel groups, each having an even number of detection pixels continuously lined up in a pitch direction of the grid, and are provided to the image output device.

In a radiation image taking apparatus of the second aspect, in the radiation image taking apparatus of the first aspect, the pitches of the grid are set to have such a relationship that when radiations are projected to the radiation detecting device through the grid, a half length of the pitch of the projection image is equal to a pitch of a detection pixel of the radiation detecting device; and there is provided an operation device wherein the radiation detection signals obtained from the radiation detecting device are subjected to an equalizing process for every two detection pixel groups continuously lined up in the pitch direction of the grid, and are provided to the image output device.

A radiation image taking apparatus of the third aspect further includes, in the radiation image taking apparatus of the first aspect, a swinging or moving device for swinging the grid in a pitch direction; and a switching device for swinging the grid when a stationary image is taken, and for fixing the grid by stopping the swinging device when a moving image is taken.

The radiation image taking apparatus of the invention operates as follows.

According to the first aspect of the invention, the grid provided to the radiation image taking apparatus has a pitch of slits such that when radiations irradiated to the sample to be measured from the radiation irradiation device are projected to the radiation detecting device through the grid, a length obtained by multiplying odd-number to a half pitch of the projection image becomes equal to a pitch of detection pixels of the radiation detecting device. Then, the radiation detection signals detected at the radiation detecting device through the grid are subjected to an equalizing process for every pixel units, each having an even number detection pixels continuously lined up in a pitch direction of the grid. That is, since the equalizing operation process is carried out with a combination, as a unit, of a high level radiation detection signal and a low level radiation detection signal from the radiation detection signals detected by the radiation detecting device, irregularity levels of the radiation detection signals can be canceled, i.e. equalized. As a result, it is possible to remove moires from an output image outputted from the image output device.

According to the second aspect of the invention, the grid used in the radiation image taking apparatus according to the first aspect is set to have a relationship such that a length of a half pitch of a projection image is equal to a pitch of a detection pixel of the radiation detecting device. Then, the radiation detection signals detected from the radiation detecting device through the grid are inputted into the operation device and subjected to an equalizing process for every two detection pixels continuously lined up in a pitch direction of the grid. That is, through the operation process for equalization by using the radiation detection signals of a two-pixel unit, a decrease in resolution can be limited to the minimum rather than equalization by using the radiation detection signals with an even-number unit more than 4 pixels.

According to the third aspect of the invention, when a stationary image is taken, the grid is swung or moved in the pitch direction with respect to the radiation detecting device. In other words, the projection image projected on the detection pixels of the radiation detecting device through the grid is made uniform, so that the radiation detection signals detected from the radiation detecting device become uniform to thereby remove moires from the output image outputted from the image output device. That is, since it is not necessary to correct the image by the operation process, an output image having a high resolution can be obtained by reducing deterioration of the output image. Also, when a moving image is taken, moires can be removed from the output image by stopping swinging of the grid through a switching device and using an operation device and the grid according to the first or second aspect.

DETAILED DESCRIPTION OF PREFERRED EMBODIMENTS

With reference to the accompanying drawings, embodiments according to the present invention are explained.

Figure 1:
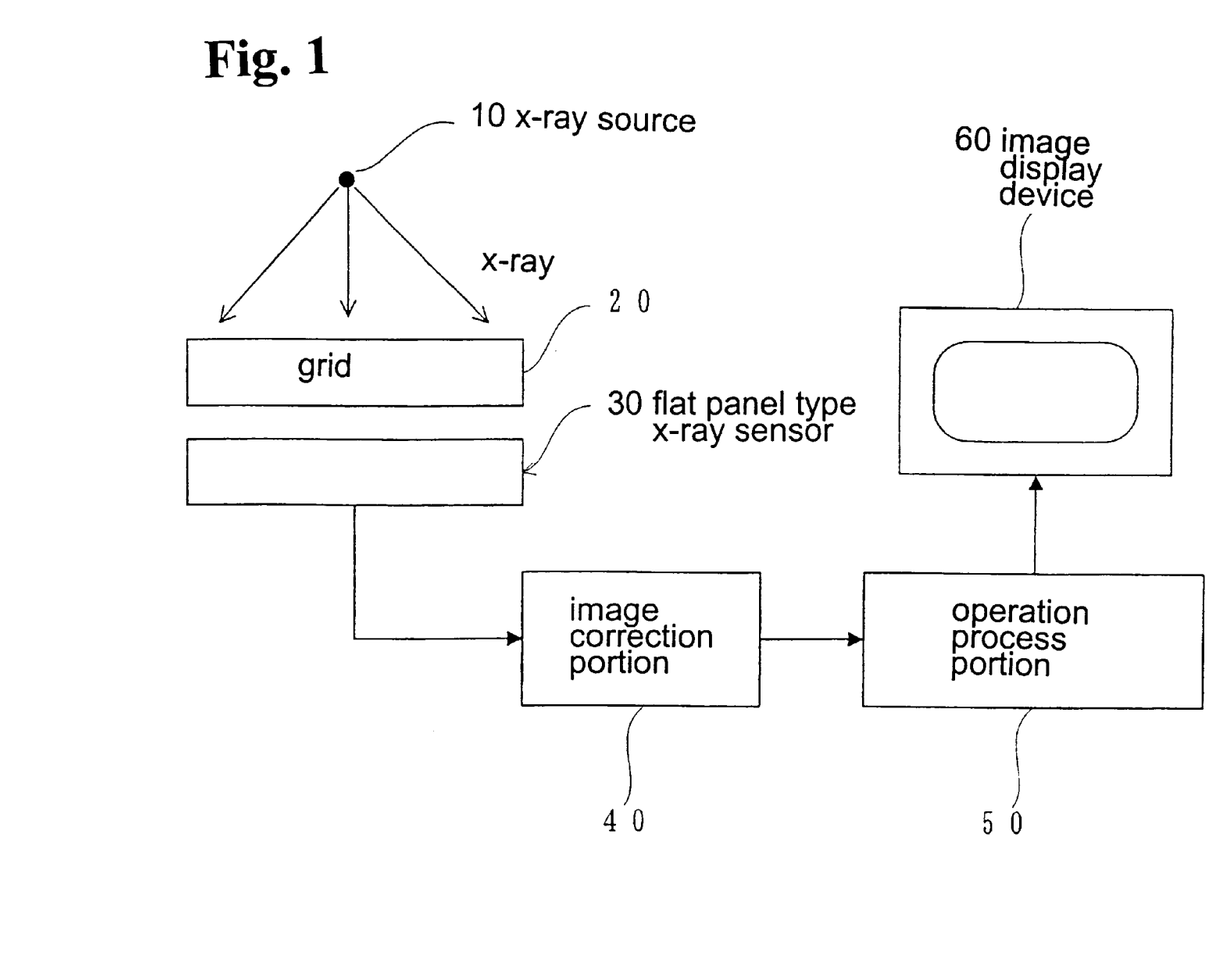
FIG. 1 is a block diagram of a radiation image taking apparatus of a first embodiment according to the invention.

FIG. 1 is a block diagram showing a first embodiment of a radiation image taking apparatus according to the present invention.

The radiation image taking apparatus of the first embodiment generally includes an X-ray source 10 for irradiating X-rays to a sample to be measured; a grid 20 for removing dispersion rays contained in the X-rays passing through the sample to be measured; a flat panel type X-ray sensor 30 for detecting the X-rays passing through the grid 20; an image correcting portion 40 for correcting a detected image outputted from the flat panel type X-ray sensor 30; an operation process portion 50 for carrying out an equalizing process of X-ray detection signals based on the X-ray detection signals outputted from the image correction portion 40; and an image displaying device 60 for outputting an image information outputted from the operation process portion 50 to display. Incidentally, the X-ray source 10 corresponds to the radiation irradiation device; the flat panel type X-ray sensor 30 corresponds to the radiation detecting device; the operation process portion 50 corresponds to the operation process device; and the image displaying device 60 corresponds to the image outputting device, of the present invention, respectively.

Hereunder, structures and functions of the respective portions are explained.

The X-ray source 10 irradiates cone-shape X-ray beams (hereinafter referred to as "X-rays") to the sample to be measured.

Figure 2:
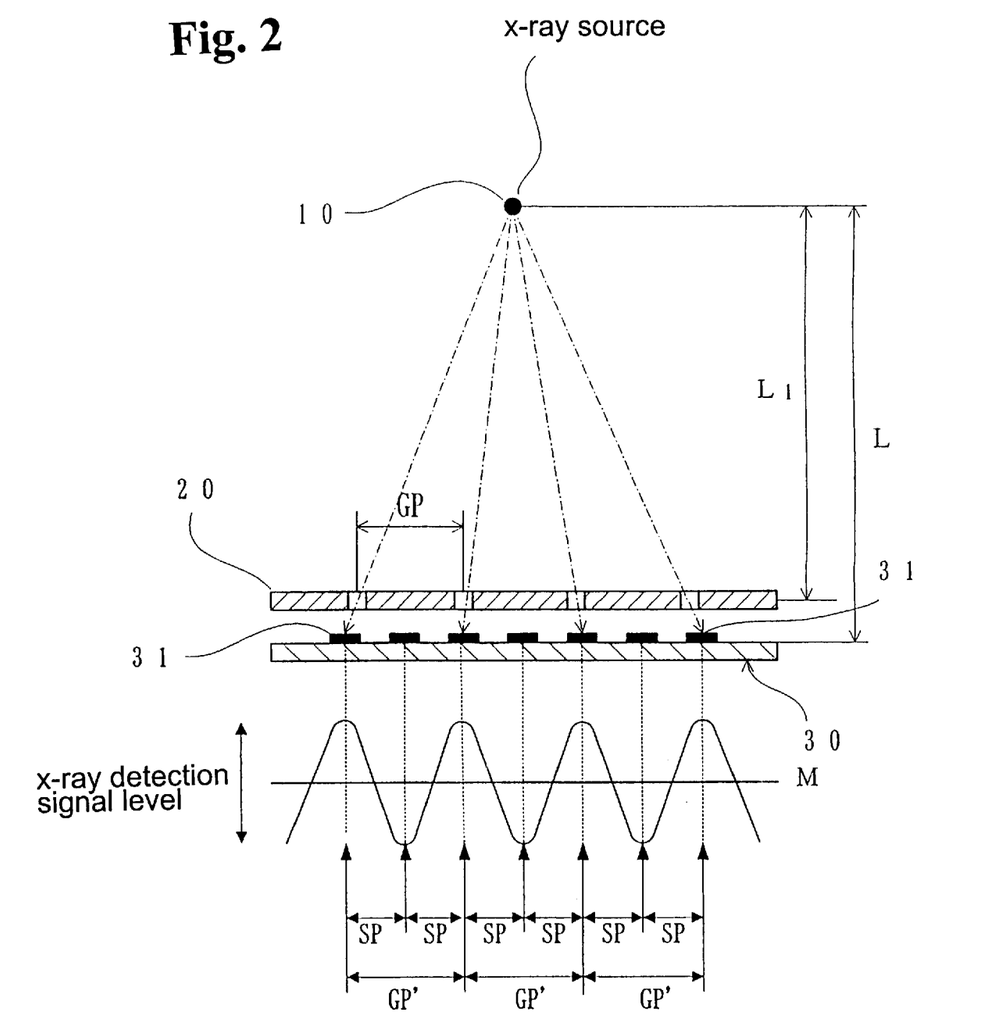
FIG. 2 is an explanatory view showing a detection theory of radiations according to the invention.

As shown in FIG. 2, when X-rays are ejected to detection pixel groups 31 of the flat panel type X-ray sensor 30 through the grid 20, the projection image is enlarged by a magnification determined by a distance $L_1$ from the X-ray source 10 to the grid 20 and a distance $L$ from the X-ray source 10 to the flat panel type X-ray sensor 30. In other words, a relationship between a pitch GP of the grid 20 and a pitch GP' of the projection image can be expressed by the following equation (1):

$$GP'=GP \cdot L/L_1 \tag{1}$$

Also, as a characteristic structure of the present invention, the pitch or length GP of the slit of the grid 20 has a relationship such that the length obtained by multiplying odd-number to a half pitch of the projection image on the X-ray sensor 30 through the grid 20 is equal to a pitch SP of detection pixels of the flat panel type X-ray sensor 30. Namely, a relationship between the pitch GP' of the projection image and the pitch SP of the detection pixel can be expressed by the following equation (2):

$$(GP'/2)(2n-1)=SP \qquad (2),$$

wherein n represents a positive integer.

More specifically, the pitch GP of the grid 20 has a relationship of the following equation (3) from the above equations (1) and (2):

$$GP=2 \cdot SP \cdot L_1/L \cdot (2n-1) \qquad (3)$$

More specifically, in the first embodiment, the pitch GP of the grid 20 is structured such that when the X-rays are projected to the flat panel type X-ray sensor 30 through the grid 20, a length of a half of the pitch GP' of the projection image is equal to the pitch SP of the detection pixels 31.

Incidentally, the pitch GP of the grid 20 or slits is not limited to the above-mentioned relationship of the present embodiment, and there may be a relationship such that a length obtained by multiplying odd-number to the half pitch GP' of the projection image, such as three times, five time, seven time . . . , is equal to the pitch SP of the detection pixels 31 of the flat panel type X-ray sensor 30.

Also, in the grid 20, there are used flakes, such as Pb (lead), W (tungsten) of a high atomic number, U (uranium), through which X-rays do not relatively pass, and Al (aluminum) for a slit portion, through which X-rays pass. Also, a size of the grid 20 is changed according to a size of the flat panel type X-ray sensor 30.

Figure 3:
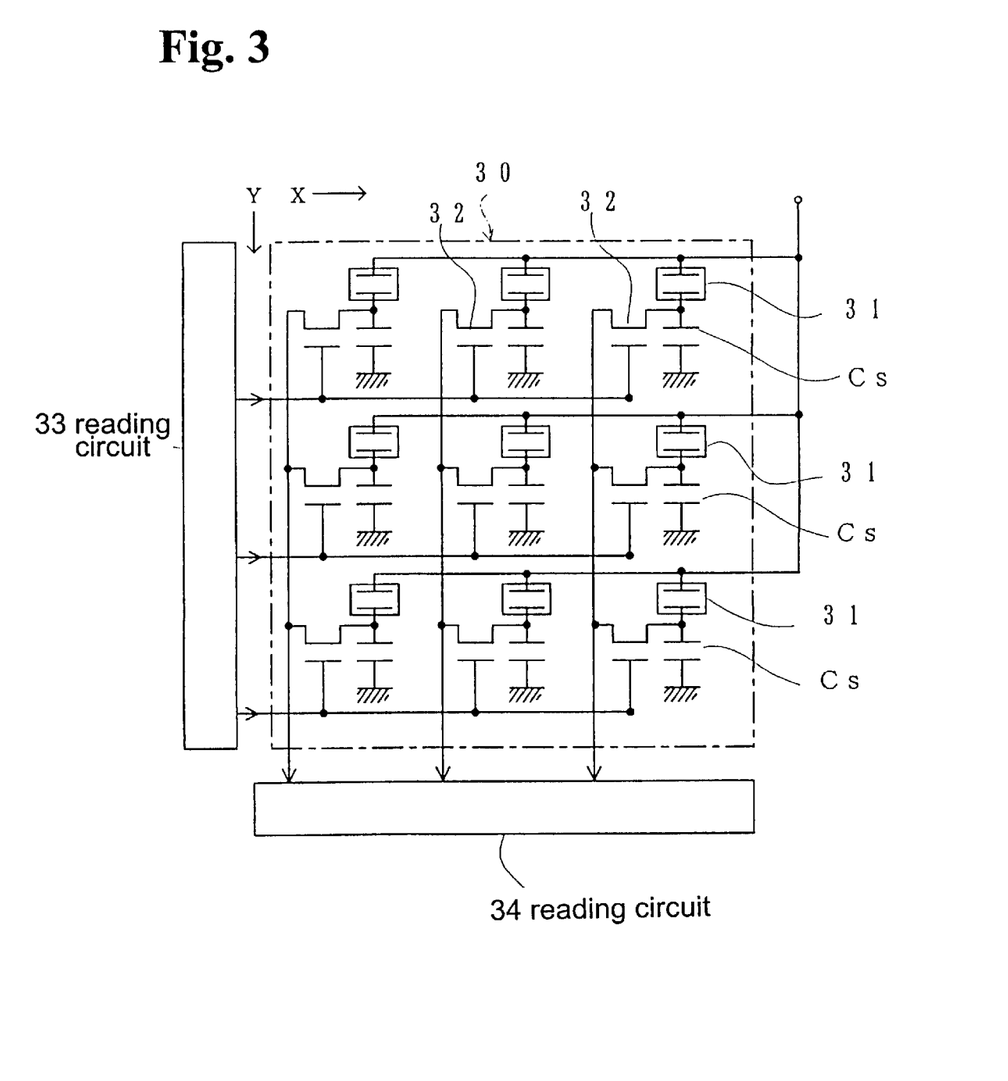
FIG. 3 is a structural diagram showing a flat panel type X-ray sensor.

The flat panel type X-ray sensor 30, as shown in FIG. 3, includes X-ray detecting base plates 31; capacitors Cs for storing collection carriers through carrier collection electrodes of the X-ray detecting base plates 31; thin film transistors as switching elements 32, which are normally in an off state, for taking out charges stored in the capacitors Cs; a reading circuit 33 in an X-axis direction; and a reading circuit 34 in a Y-axis direction.

Incidentally, although FIG. 3 shows a matrix structure consisting of only nine in total, i.e. 3 in a lengthwise direction and 3 in a widthwise direction for the sake of convenience, if necessary, for example, practically, a matrix has a structure of 1024 in a lengthwise direction and 1024 in a widthwise direction.

The image correcting portion 40 carries out an operation process through filtration to remove artifacts and the like generated on a detection image.

Figure 4:
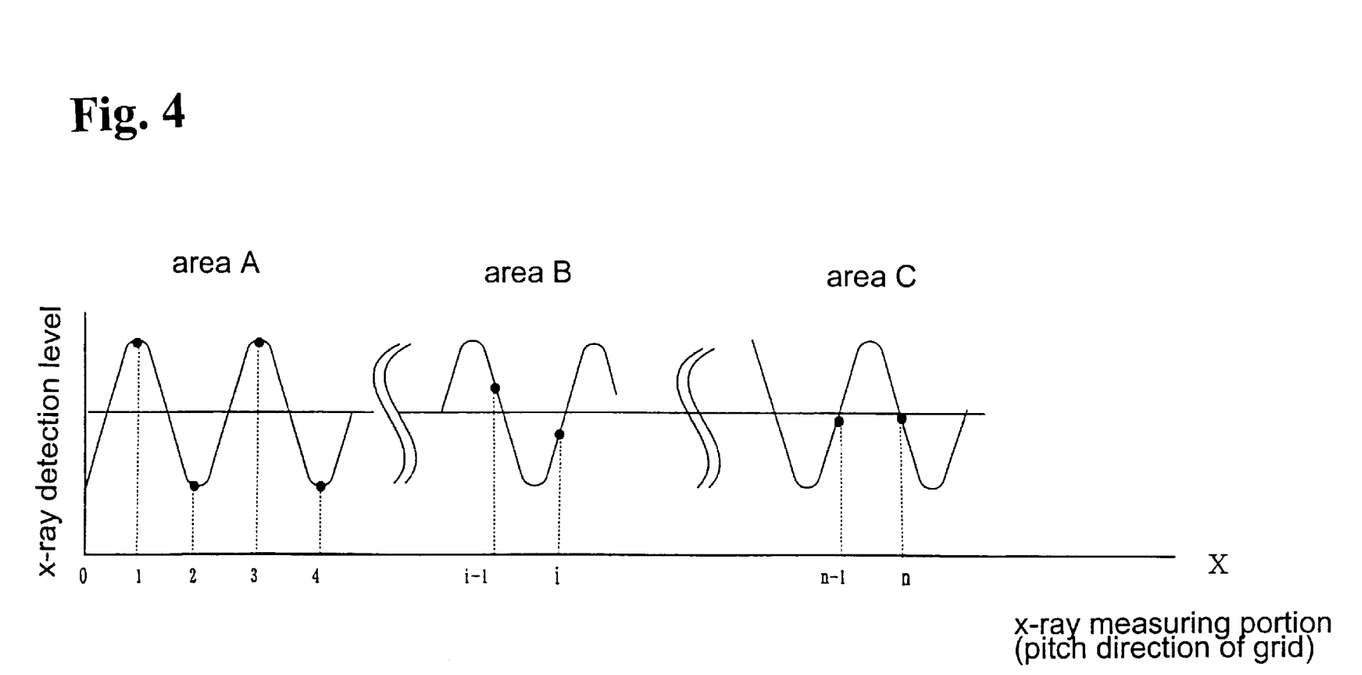
FIG. 4 is a graph showing X-ray detection signals detected by the radiation image taking apparatus of the first embodiment of the invention.

The operation process portion 50, as shown in FIG. 4, equalizes the irregularities of levels of X-ray detecting signals by carrying out the operation process through addition average or moving average with a two-pixel unit of the detection pixels, i.e. signs on an X-axis in the drawing, continuously lined up in a pitch direction of the grid based on the X-ray detection signals outputted from the image correction portion 40. Incidentally, the addition average and moving average are not limited to those of the two-pixel unit, and they may be carried out with a detection pixel group unit of even number continuously lined up in the pitch direction of the grid.

The image displaying device 60 displays image information subjected to the operation process, such as various corrections.

Incidentally, the image output device according to the present invention is not limited to the image displaying device 60, and it may be a light sensitive substance, such as a printer and a film.

Next, operations of the radiation image taking apparatus of the present embodiment as described above are explained.

As shown in FIG. 2, X-rays irradiated from the X-ray source 10 and passing through the sample to be measured pass through slits for the respective pitches GP provided on the grid 20 and are projected to the detection pixel groups 31 on the flat panel type X-ray sensor 30.

The projected images detected at the detection pixel groups 31 are carrier-converted by the flat panel type X-ray sensor 30 and stored in the respective capacitors Cs. Then, the stored carriers are properly outputted to the image correction portion 40 for filtering, and the pixel information, artifacts of which are removed, is outputted to the operation process portion 50.

The image information inputted into the operation process portion 50, for example, as shown in FIG. 4, is subjected to an addition average process or moving average process with two pixels, as a unit, of the detection image group 31 continuously lined up in the pitch direction of the grid 20 (in the drawing, X-axis plus direction). In other words, assuming that a level of the X-ray detection signal detected from each detection pixel is Sn (n represents a detection pixel number and is positive integer), the two-pixel addition average in an area A becomes an average of levels S1 and S2 of the X-ray detection signals of the first and second detection pixels. An average value obtained through the operation process is assigned to the first and second detection pixels. Also, in an area B, an average value of levels Si−1 and Si of the X-ray detection signals from the detection pixels of the i−1st and i-th is assigned to the respective detection pixels; and in an area C, an average value of levels Sn−1 and Sn of the X-ray detection signals from the detection pixels of the n−1st and n-th is assigned to the respective pixels. As a result, the irregularities in levels of the X-ray detection signals caused by the grid 20 can be solved.

Also, the two-pixel moving average is obtained such that, among levels Sn of the X-ray detection signals detected from the respective detection pixels, in the area A, an equalizing process of the levels S1 and S2 of the X-ray detection signals of the first and second detection pixels is carried out; the obtained average value is assigned to the first detection pixel; then, an equalizing process of the levels S2 and S3 of the X-ray detection signals of the second and third detection pixels is carried out; and the obtained average value is assigned to the second detection pixel. The two-pixel moving average as described above is carried out from area A to area C. As a result, irregularities of the levels of the X-ray detection signals can be solved. Further, by the two-pixel moving average, an output image having a higher resolution than that of the two-pixel addition average can be obtained.

Incidentally, in the present embodiment, for the sake of explanatory convenience, although it is assumed that the X-ray detection signal levels are uniform, actually, the values obtained from the equalizing process are superposed on the detected X-ray detection signal levels of the sample to be measured.

Figure 5:
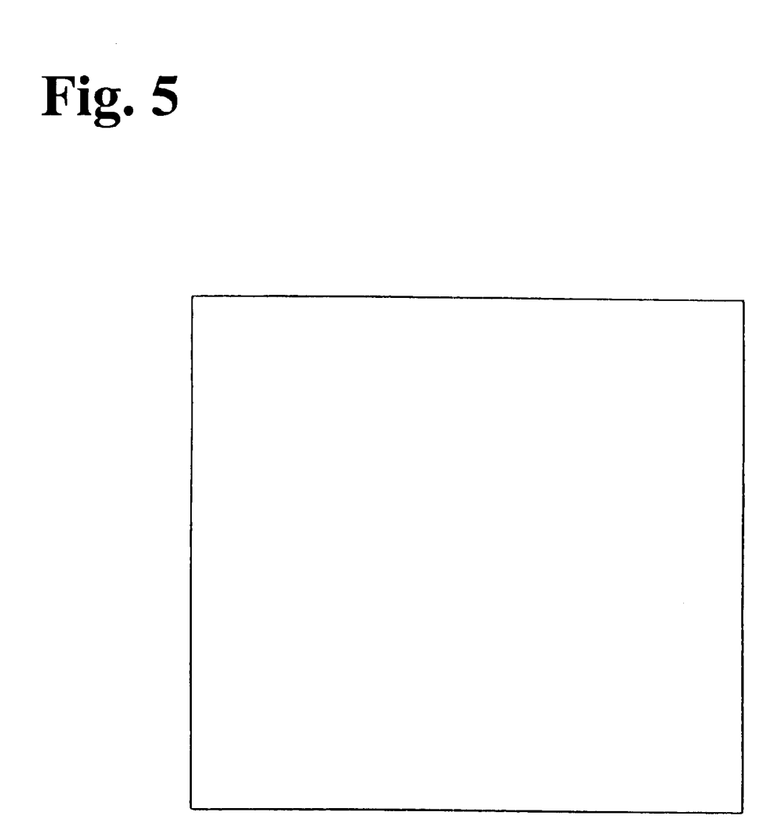
FIG. 5 is an output image outputted from the radiation image taking apparatus of the invention.

The image information, in which irregularities in the X-ray detection signal levels have been equalized at the operation process portion 50, is outputted to the image displaying device 60. At this time, as shown in FIG. 5, moires caused by the irregularities in the X-ray detection signal levels have been removed, and a clear image can be displayed.

By the way, in the present embodiment, after the image correction is carried out at the image correction portion 40, the operation process is carried out at the operation process portion 50 to remove moires. However, after moires are removed, filtering of the structural images may be made at the image correction portion 40.

Figure 6:
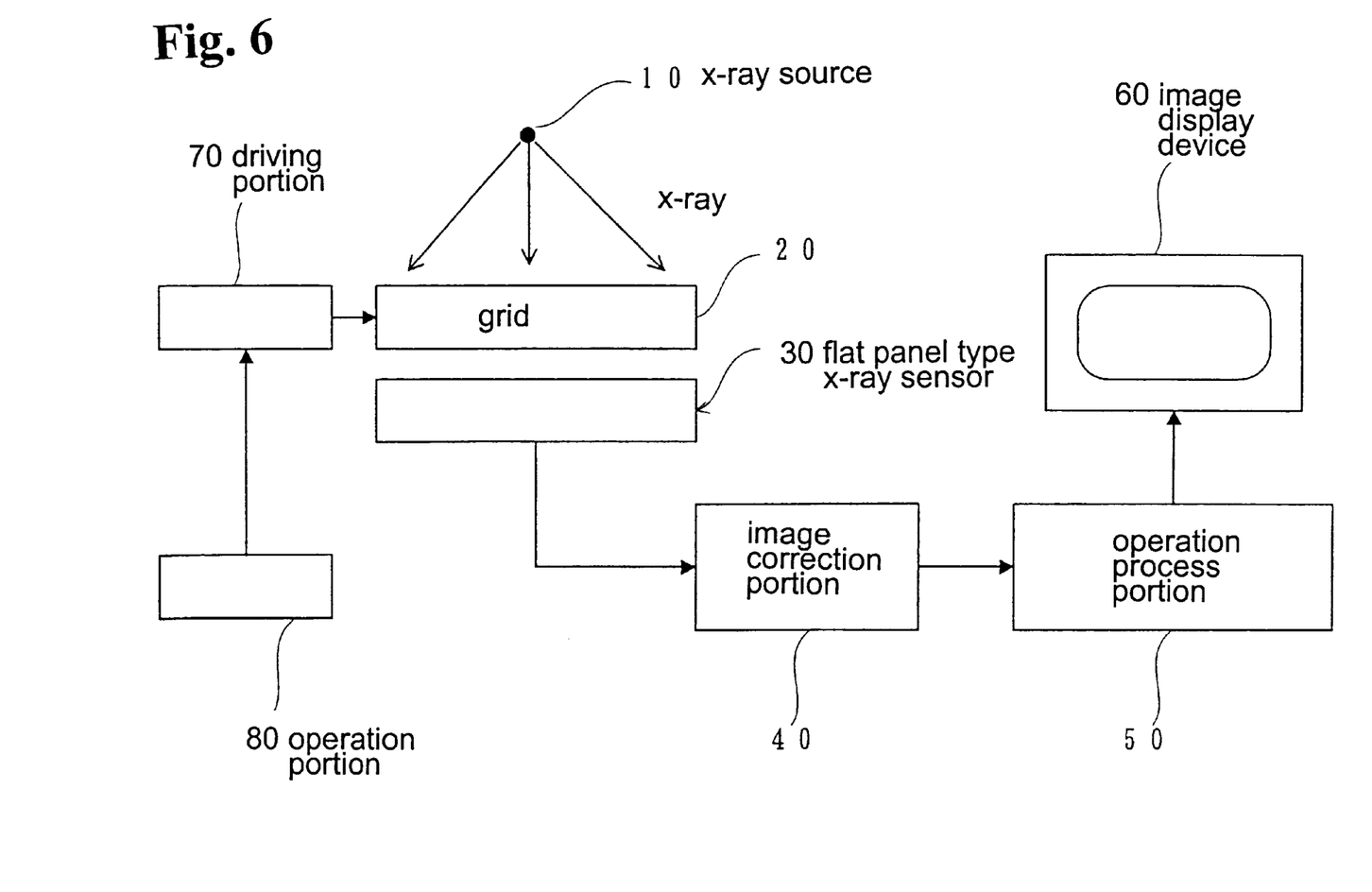
FIG. 6 is a block diagram of a radiation image taking apparatus of a second embodiment according to the invention.

FIG. 6 is a block diagram of a second embodiment of the radiation image taking apparatus according to the present invention.

Characteristics of the present embodiment, as shown in FIG. 6, reside in that a driving portion 70 for swinging or moving the grid 20, and an operation portion 80 for operating the driving portion 70 are included.

In case a stationary image is taken, the driving portion 70 horizontally swings the grid 20 while facing the flat panel type X-ray sensor 30 in the pitch direction. Thus, it is possible to prevent a resolution of the output image from being reduced by removing moires through the swinging of the grid 20. In other words, in case moires are removed through the equalizing process of a plurality of pixel units, since levels of the equalized X-ray detection signals are assigned to the respective detection pixels to be operated, the levels are slightly deteriorated when compared with the levels of the original X-ray detection signals detected from the respective detection pixels. In order to prevent such a resolution from being lowered, the grid 20 is swung or moved. In case of the stationary picture, since it is not necessary to swing or move the grid 20 at a high speed as in a moving image, it is not required to enlarge a structure of the device so much.

Also, in case the moving image is taken, the grid 20 is not swung, and is fixed as in the first embodiment described above. Thus, since it is not required to forcibly swing the grid 20 at a high speed, a good moving image without moires can be taken. Incidentally, the driving portion 70 corresponds to the swinging device of the present invention.

The operation portion 80 makes a switching operation in accordance with the stationary image or moving image taking condition. By the way, the operation portion 80 corresponds to the switching device of the grid 20. Since the other structures are the same as those of the first embodiment, explanations of the same are omitted.

While the grid 20 in the present embodiment is used for taking images of both stationary image and moving image, in case the grids are provided separately, it is not necessary to use the grid 20 of the invention for the stationary image, and the pitch on the grid can be suitably set.

The present invention is not limited to the above-described embodiments and can be modified as described below.

An X-ray source 10 for outputting fan beams, a grid 20 and an X-ray detecting device having a one-dimensional matrix arrangement disposed to face the X-ray source 10 with respect to a sample to be measured therebetween may scan the sample to be measured.

By using an X-ray source 10 for outputting cone beams, a grid 20 and an X-ray detecting device having a one-dimensional matrix arrangement may scan an area of a sample to be measured to which the cone beams are irradiated.

The radiation detecting device is not limited to the flat panel type X-ray sensor 30. It may be a solid state image-taking element, such as a charge-coupled device (CCD).

As apparent from the above description, according to the radiation image taking apparatus of the first aspect of the invention, when radiations are projected to the radiation detecting device through the grid, the radiation image is taken by using the grid having such a relationship that a length obtained by multiplying odd-number to a half pitch of a projection image on the radiation detecting device through the grid is equal to a pitch of detection pixels of the radiation detecting device. Then, the radiation detection signals detected from the detection pixels of the radiation detecting device through the grid are subjected to an equalizing process for every pixel groups, each having an even number of detection pixels, continuously lined up in a pitch direction of the grid to thereby remove moires from the output image outputted from the output image device. Even if the positions of the pitches of the slits on the grid and pitches of the detection pixels are slightly displaced, since the equalizing process is carried out with a combination, as a unit, of a high level radiation detection signal and a low level radiation detection signal from the respective even-number detection pixels lined up in the pitch direction of the grid, irregularities of the radiation detection signals can be reduced to a sufficiently practical level. As a result, it is not necessary to keep the pitches of the grid accurately, so that the radiation image taking apparatus can be made economical. Further, since the grid can be fixedly disposed without swing, the apparatus can be miniaturized.

According to the radiation image taking apparatus of the second aspect of the invention, the grid used in the radiation image taking apparatus of the first aspect is set to have such a relationship that when radiations are projected to the radiation detecting device through the grid, a length of a half pitch of a projection image is equal to a pitch of a detection pixel of the radiation detecting device. Then, the radiation detection signals detected by the radiation detecting device through the grid are inputted into the operation device, and the equalizing process is carried out for every two detection pixel groups continuously lined up in the pitch direction of the grid to thereby keep reduction in a resolution of the output image outputted from the image output device to a minimum.

According to the radiation image taking apparatus of the third aspect of the invention, when a stationary image is taken, since it is not necessary to swing the swinging device at a high speed as in case of taking a moving image, the grid is swung in its pitch direction with respect to the radiation detecting device. In other words, with use of the swinging device, it is not necessary to make corrections by the operation device to thereby prevent a resolution of the output image from being lowered. Also, when a moving image is taken, since it is not required that the grid is forcibly swung at a high speed by stop swinging of the grid with a switching device, a good moving image can be taken and moires can be removed from the output image outputted from the output device.

While the invention has been explained with reference to the specific embodiments of the invention, the explanation is illustrative and the invention is limited only by the appended claims.

What is claimed is:

1. A radiation image taking apparatus comprising:
   a radiation irradiation device for irradiating radiation to a sample to be measured,
   a grid having a number of slits for allowing the radiation to pass therethrough, said slits being formed with a predetermined pitch for removing dispersion rays formed when the radiation passes through the sample to be measured,
   a radiation detecting device situated near the grid and having a plurality of detection pixels with a pitch for detecting the radiation passing through the slits of the grid, said detection pixels being arranged such that when the radiation is projected to the radiation detecting device through the grid, a length obtained by multiplying an odd-number to a half pitch of a projection image on the radiation detecting device through the slits of the grid is equal to the pitch of the detection pixels of the radiation detecting device, an operation device electrically connected to the radiation detecting device, and operating such that radiation detection signals obtained from the radiation detecting device is subjected to an equalizing process for every pixel group, each being formed of even number of the detection pixels continuously lined up in a pitch direction of the grid, and an image output device electrically connected to the operation device for receiving signals by the equalizing process and outputting a detected image.

2. A radiation image taking apparatus as claimed in claim 1, wherein said detection pixels are arranged in one dimensional form or two dimensional form.

3. A radiation image taking apparatus as claimed in claim 1, wherein said pitch of the slits on the grid is set such that when the radiation is projected to the radiation detecting device through the grid, a length of a half pitch of the projection image is equal to the pitch of the detection pixels of the radiation detecting device, said radiation detection signals obtained from the radiation detecting device being subjected to the equalizing process for every two detection pixel groups continuously lined up in the pitch direction of the grid.

4. A radiation image taking apparatus as claimed in claim 1, further comprising a swinging device for swinging the grid in a pitch direction, and a switching device electrically connected to the swinging device for swinging the grid by actuating the swinging device when a stationary image is taken, and for fixing the grid by stopping the swinging device when a moving image is taken.

5. A radiation image taking apparatus as claimed in claim 1, wherein said odd-number to be multiplied is one number selected from 3, 5 and 7.

6. A radiation image taking apparatus as claimed in claim 1, wherein in the equalizing process, signals of the pixels in one group are equalized by one of an addition average and a moving average.

* * * * *